United States Patent

Shirayanagi

[11] Patent Number: 4,469,413
[45] Date of Patent: Sep. 4, 1984

[54] ASPHERICAL LENS FOR INDIRECT OPHTHALMOSCOPE

[75] Inventor: Moriyasu Shirayanagi, Tokyo, Japan

[73] Assignee: Asahi Kogaku Kogyo Kabushiki Kaisha, Tokyo, Japan

[21] Appl. No.: 425,583

[22] Filed: Sep. 28, 1982

[30] Foreign Application Priority Data

Dec. 22, 1981 [JP] Japan ................... 56-208726

[51] Int. Cl.³ .................... A61B 3/12; G02B 13/18
[52] U.S. Cl. ........................... 350/432; 351/205
[58] Field of Search .................. 350/432; 351/205

[56] References Cited

U.S. PATENT DOCUMENTS 3,914,032 10/1975 Takano et al. ................ 350/432
4,222,634 9/1980 Muchel ...................... 350/432

*Primary Examiner*—John K. Corbin
*Assistant Examiner*—Scott J. Sugarman
*Attorney, Agent, or Firm*—Sughrue, Mion, Zinn, Macpeak & Seas

[57] ABSTRACT

An aspherical lens for an indirect ophthalmoscope, comprising a single biconvex lens having a first surface with a radius of curvature $r_1$, and a second aspherical surface facing the examiner and having a paraxial radius of curvature $r_2$. The lens being constructed to meet the following requirements:

$$-0.65 < \frac{r_2}{r_1} < -0.35 \quad (1)$$

$$1 - 3x^2 < \frac{d^2y}{dx^2} < 1 - 1.4x^3 \quad \left(0 \leq x \leq -\frac{D}{2r_2}\right) \quad (2)$$

where D is the effective diameter of the lens, y is the displacement in the direction of an optical axis of an aspherical shape as expressed by a rectangular coordinate system having the origin at the vertex of the second surface and normalized by $r_2$, and x is the displacement in a direction normal to the optical axis and also normalized by $r_2$.

4 Claims, 10 Drawing Figures

ASPHERICAL LENS FOR INDIRECT OPHTHALMOSCOPE

BACKGROUND OF THE INVENTION

The present invention relates to an improvement in an aspherical lens for an indirect ophthalmoscope One type of indirect ophthalmoscope employed in medical treatment of eyes comprises, as shown in the FIG. 1, a condenser lens 2 and an aspherical lens 3 for causing a bundle of rays omitted from a light source 1 to converge in the vicinity of the pupil of an eye 4 being examined. As illustrated in FIG. 2, an image of the fundus of the eye 4 is focused by the optical system of the eye being examined and the aspherical lens 3 on a position 5 in space, the focused image being observed by the examiner through an eyepiece 6. The aspherical lens 3 may be utilized as a magnifier to examine an object 8 at an anterior portion, the object 8 being observed as a virtual image 9, as shown in FIG. 3.

Conventional aspherical lenses have spherical aberration and coma relatively well compensated for or corrected so as to be usable in an illumination optical system, and also have relatively well corrected for distortion for use as a magnifier optical system. Spherical aberration and coma under the conjugate condition for pupils (in which the pupil of the eye 4 being examined and that of an eye 7 of the examiner are in conjugate positions) when used as an observation optical system, can also be compensated for when the spherical aberration and coma for the illumination system have been corrected. However, the astigmatism of the lens used as the observation optical system has not been corrected to a substantial degree. When the fundus image is observed by the examiner with the unaided eye, as shown in FIG. 2, the ray of light is limited by the pupil of the examiner's eye 7. Because of the accommodation of the examiner's eye 7 and the increased depth of field, thre has been no need for substantially correcting the astigmatism. Where an optical system utilizing an indirect ophthalmoscope is used, as illustrated in FIG. 4, to form a fundus image at a position 5 in space, and such a fundus image is photographed by a film 12 through a semitransparent mirror 10 and a photographic optical system 11, good picture quality has not been obtained with the prior aspherical lenses.

SUMMARY OF THE INVENTION

It is an object of the present invention to provide an aspherical lens having sufficiently improved optical performance when used as a system for illuminating a fundus, an optical system for observing an eye, and a magnifying optical system, and also having sufficiently improved optical performance when used as a photographic optical system.

DESCRIPTION OF THE PREFERRED EMBODIMENTS

The present invention will now be described in detail.

The aspherical lens according to the present invention comprises a single biconvex lens having an aspherical surface facing the examiner, the aspherical lens satisfying the following requirements:

$$-0.65 < \frac{r_2}{r_1} < -0.35 \quad (1)$$

$$1 - 3x^2 < \frac{d^2y}{dx^2} < 1 - 1.4x^3 \left( 0 \leq x \leq -\frac{D}{2r_2} \right) \quad (2)$$

Figure 5:
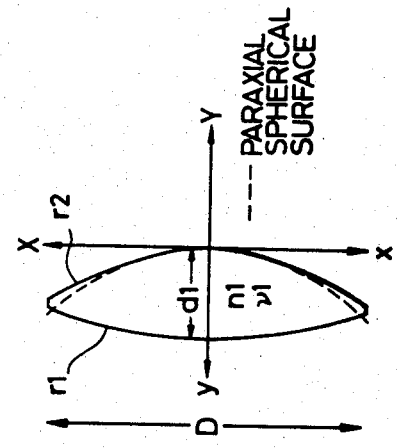
FIG. 5 is a diagram showing a cross section of an aspherical lens according to the present invention and a coordinate system defining an aspherical shape.
Figure 7:
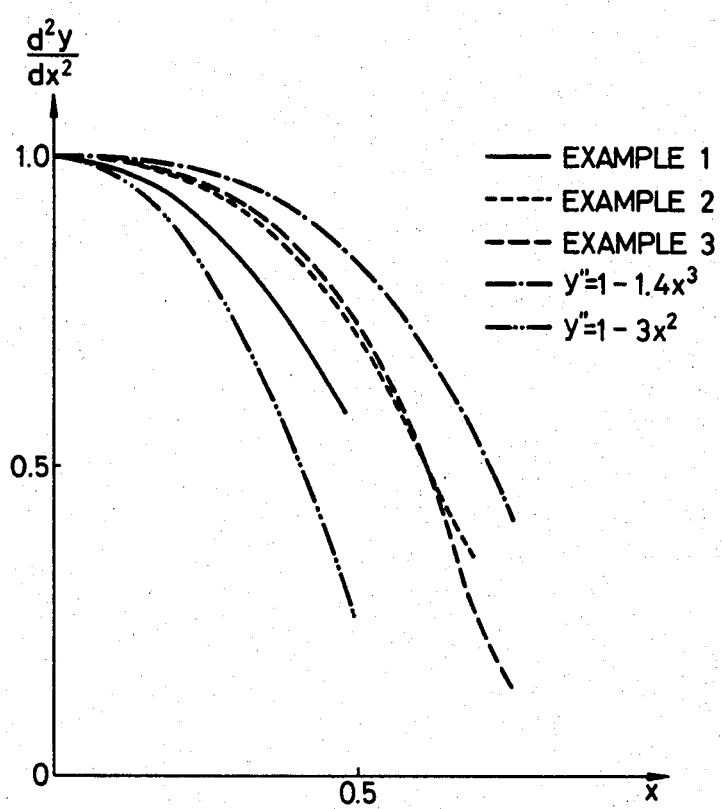
FIG. 7 is a graph showing quadratic differential coefficients of the shapes of aspherical lenses according to first, second and third Examples of the present invention.
Figure 8:
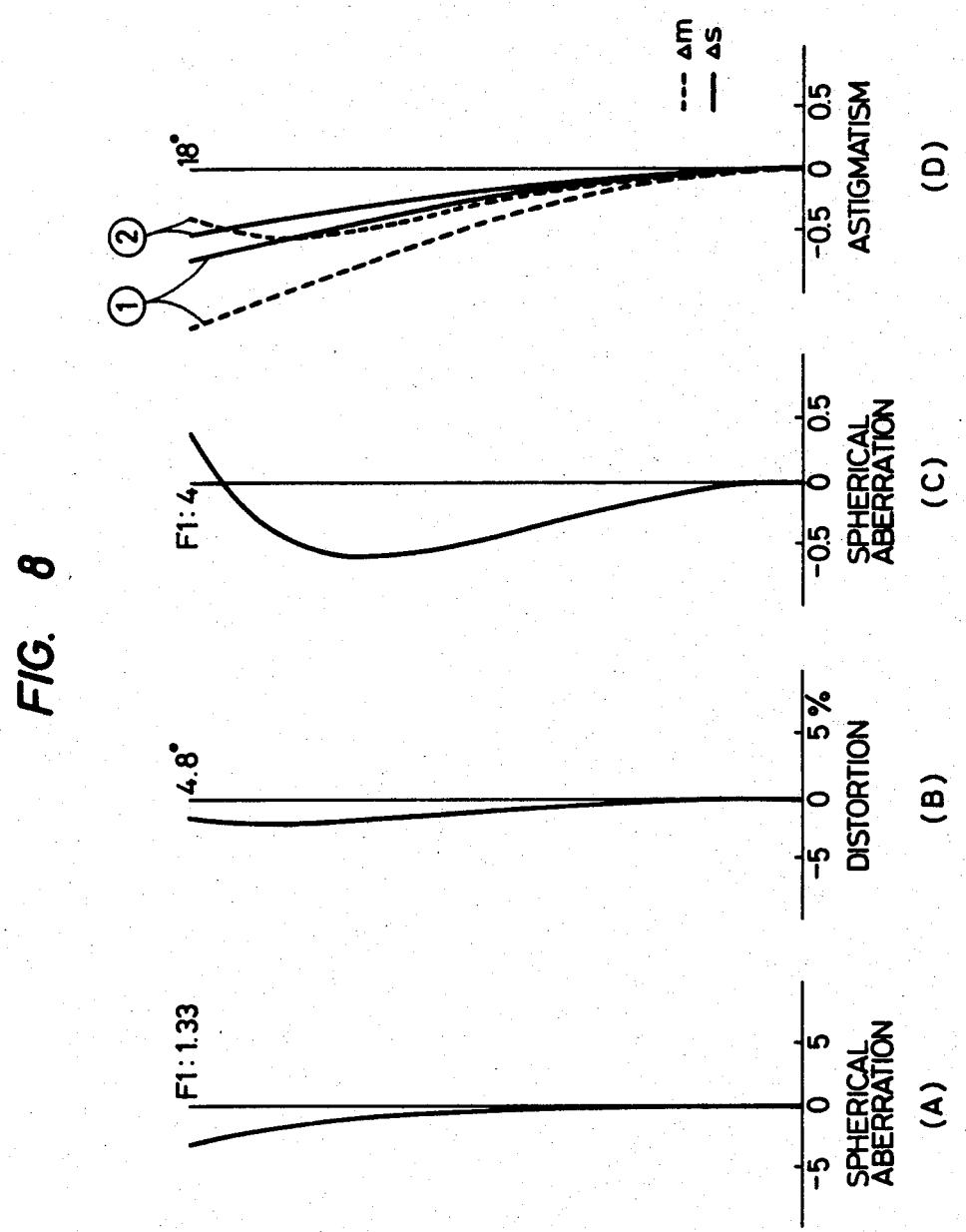
FIGS. 8, 9 and 10 are diagrams illustrative of aberrations of the aspherical lenses according to the first, second and third Examples, (A) showing spherical aberration of the illumination optical system, (B) showing distortion of the magnifier optical system, (C) showing spherical aberration of the photographic optical system having an aspherical lens and a photographic lens, (D) showing astigmatism of the photographic optical system having an aspherical lens and a photographic lens, the curve 1 representing a conventional aspherical lens and 2 an aspherical lens according to the present invention.
Figure 9:
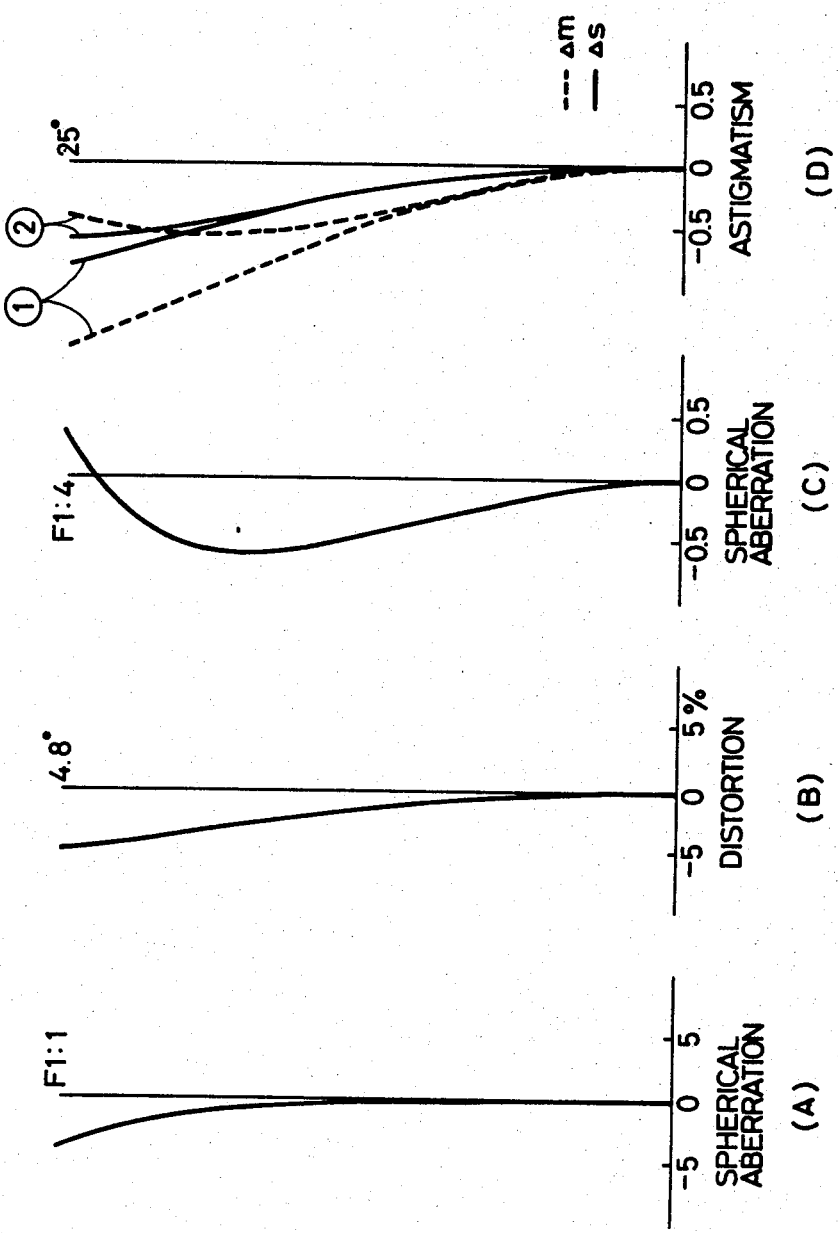
Figure 10:
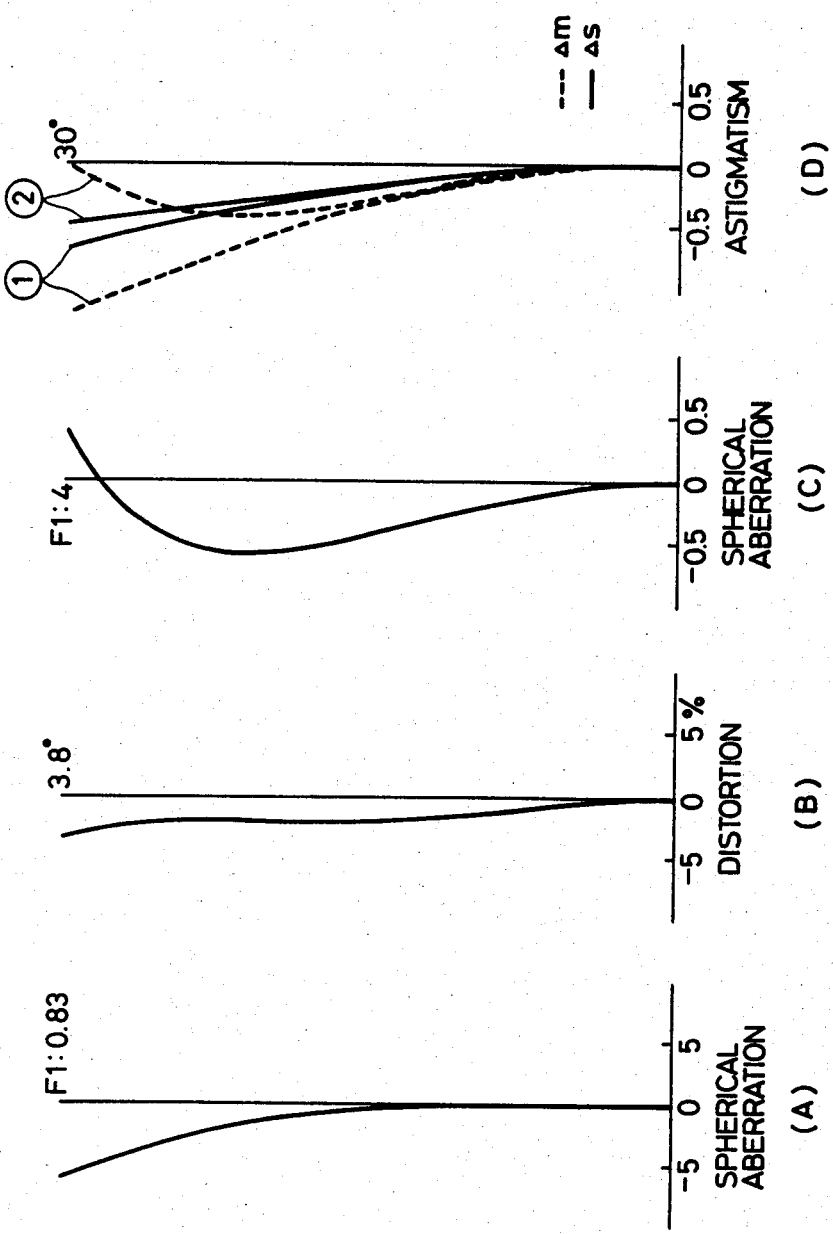

FIG. 5 shows such a lens in cross section. The symbols or letters in the above requirements are defined as follows:

$r_1$: the radius of curvature of the first surface;

$r_2$: the paraxial radius of curvature of the second surface;

D: the effective aperture;

$x = X/r_2$, $y = Y/r_2$

X: the displacement in a direction normal or perpendicular to the optical axis, and Y: the displacement from the vertex of the second surface toward the optical axis.

The foregoing requirements will now be described.

Requirement (1) determines the ratio of the radius of curvature of the first surface to that of the second surface. If the upper limit of the first requirement were exceeded, then the spherical aberration in the illumination optical system would not sufficiently be corrected, and the image plane in the observation and photographic optical systems would be curved in the direction of positive curvature. If the lower limit of requirement (1) were exceeded, then the distortion in the magnifier optical system would be increased in a negative direction, and the image plane in the observation and photographic optical systems would be curved in the direction of negative curvature. Thus, the desired results would not be obtained in either case. For balanced correction of various aberrations, it is necessary that the ratio between the radii of curvature of the first and second surfaces fall within the range defined by requirement (1).

Requirement (2) is concerned with the aspherical configuration of the lens, and determines the range of a quadratic differential coefficient $d^2y/dx^2$ of the aspherical shape as the shape of the second surface is expressed by way of a coordinate system (x, y) normalized by the paraxial radius of curvature of the second surface. If the upper limit of range of the requirement (2) were exceeded, then the illumination optical system would not have sufficiently corrected spherical aberration, the magnifier optical system would have its distortion increased in a positive direction, and the observation and photographic optical system would have its image plane curved in the direction of negative curvature. If the lower limit of the range of requirement (2) were exceeded, then the spherical aberration of the illumination optical system would be overly compensated for, the distortion of the magnifier optical system would be increased in a negative direction, and the image plane in the observation and photographic optical system would be curved in the direction of positive curvature. Therefore, the various aberrations would become poorer. Accordingly, correction of the aberrations requires the lens to meet requirement (2) as well as requirement (1).

When the fundus image is observed or photographed, the illumination light is reflected by the aspherical lens and the reflected light appears as two bright spots. Since the indirect ophthalmoscope optical system has no means for removing such bright spots, the lens used should preferably be a single lens to thereby reduce the number of reflecting surfaces. No single spherical lens can effect balanced correction of aberrations, and hence the lens needs to have at least one aspherical surface. Where the surface facing the eye being examined is aspherical, unsatisfactory results can be obtained. The cost of manufacture restricts the lens from having both surfaces of aspherical shape.

Accordingly, the present invention provides an aspherical lens having its optical performance retained when used as a system for illuminating a fundus, an optical system for observing an eye, and a magnifying optical system, while providing sufficiently improved optical performance when used as a photographic optical system.

Figure 1:
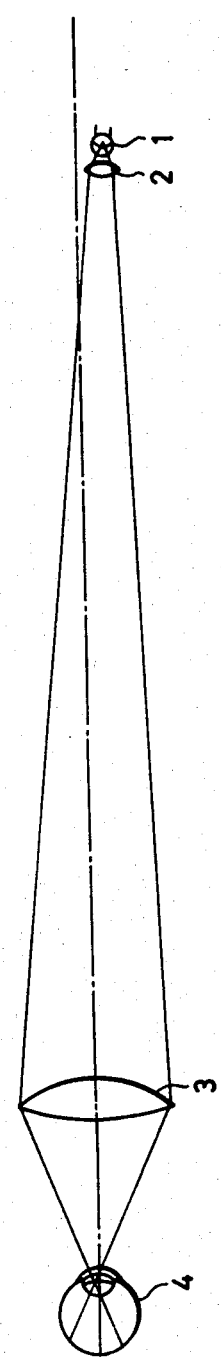
FIG. 1 is a diagram illustrative of an illumination optical system.
Figure 2:
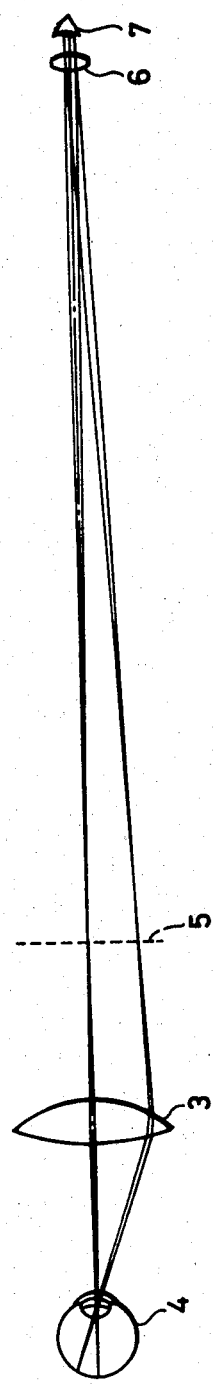
FIG. 2 is a diagram illustrative of an observation optical system in which observation is made by eye.
Figure 3:
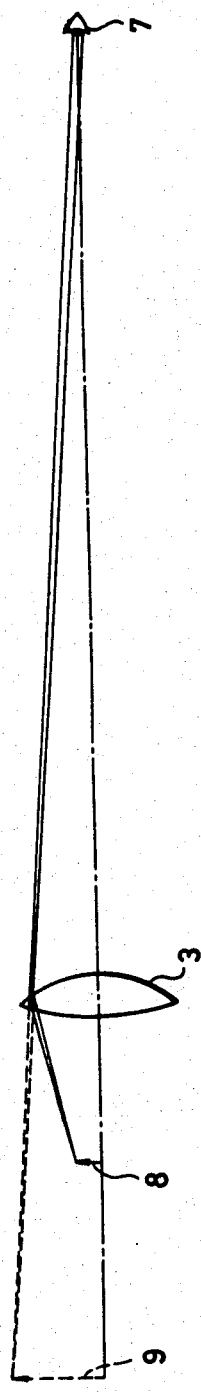
FIG. 3 is a diagram illustrative of a magnifier optical system.
Figure 4:
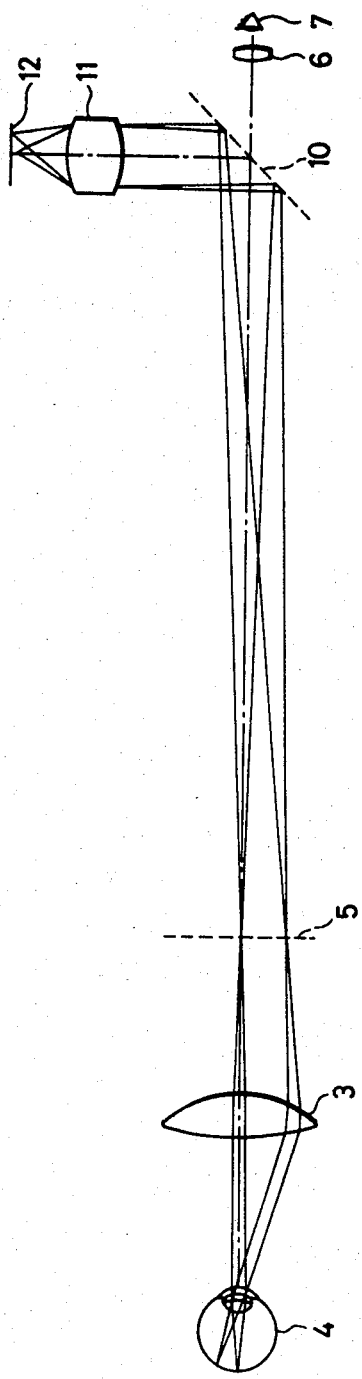
FIG. 4 is a diagram showng an observation optical system including a photographic optical system.
Figure 6:
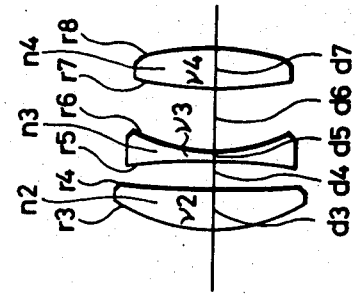
FIG. 6 is a cross-sectional view of a photographic lens used in the present invention.

Described below are first, second and third Examples of the aspherical lens according to the present invention, and various constants of a photographic lens (shown in cross section in FIG. 6). The aspherical lenses given in the Examples are symmetrical with respect to an axis of rotation and can be expressed by the equation described below. However, the aspherical lens according to the present invention should not be interpreted as being limited to those defined by this equation.

$$Y = \frac{CX^2}{\sqrt{1 - KC^2X^2}} + \sum_{i=2}^{5} A_{2i}X^{2i} \quad \left(C = \frac{1}{r_2}\right)$$

|  | First Example | Second Example | Third example |
|---|---|---|---|
| $r_1$ | 138.450 | 156.588 | 185.340 |
| $d_1$ | 16.800 | 28.400 | 36.600 |
| $n_1$ | 1.51633 | 1.51633 | 1.58913 |
| $\nu_1$ | 64.1 | 64.1 | 61.0 |
| $r_2$ | −78.939 | −72.276 | −80.040 |
| K | 1.0 | 1.0 | 1.0 |
| $A_4$ | $0.5123 \times 10^{-6}$ | $0.4960 \times 10^{-6}$ | $0.3715 \times 10^{-6}$ |
| $A_6$ | $0.1160 \times 10^{-9}$ | $0.5584 \times 10^{-10}$ | $0.2021 \times 10^{-10}$ |
| $A_8$ | $-0.7421 \times 10^{-13}$ | $0.6669 \times 10^{-14}$ | $0.6027 \times 10^{-14}$ |
| $A_{10}$ | $0.2134 \times 10^{-16}$ | $0.2480 \times 10^{-18}$ | $0.1153 \times 10^{-18}$ |
| f | 100.00 | 100.000 | 100.00 |
| $F_{NO}$ | 1:1.33 | 1:1.00 | 1:0.83 |

-continued $$Y = \frac{CX^2}{\sqrt{1 - KC^2X^2}} + \sum_{i=2}^{5} A_{2i}X^{2i} \quad \left(C = \frac{1}{r_2}\right)$$

| $\omega$ | ±18° | ±25° | ±30° |
|---|---|---|---|
| $r_2/r_1$ | −0.57 | −0.46 | −0.43 |

Photographic lens

| $r_3$ | 30.321 | | | | |
|---|---|---|---|---|---|
| | | $d_3$ | 7.009 | $n_2/\nu_2$ | 1.62230/53.2 |
| $r_4$ | 366.477 | | | | |
| | | $d_4$ | 4.005 | | |
| $r_5$ | −117.143 | | | | |
| | | $d_5$ | 2.002 | $n_3/\nu_3$ | 1.67270/32.1 |
| $r_6$ | 30.271 | | | | |
| | | $d_6$ | 9.792 | | |
| $r_7$ | 70.868 | | | | |
| | | $d_7$ | 6.007 | $n_4/\nu_4$ | 1.58267/46.4 |
| $r_8$ | −70.868 | | | | |
| f | 100.000 | | | | |
| $F_{NO}$ | 1:4.00 | | | | |
| $\omega$ | ±4° | | | | | where
 $r_i$: the radius of curvature of the ith lens;
 $d_i$: the inter-surface distance of the ith lens;
 $n_i$: the refractive index of the ith lens at d-line;
 $\nu_i$: the Abbe number of the ith lens;
 K, Ai: the aspherical coefficients;
 f: the focal length;
 $F_{NO}$: the F number; and
 $\omega$: the half angle of view.

What is claimed is:

1. An aspherical lens for an indirect ophthalmoscope, comprising a single biconvex lens having a first surface with a radius of curvature $r_1$, and a second aspherical surface facing the examiner and having a paraxial radius of curvature $r_2$, said lens being constructed to meet the following requirements:

$$-0.65 < \frac{r_2}{r_1} < -0.35 \tag{1}$$

$$1 - 3x^2 < \frac{d^2y}{dx^2} < 1 - 1.4x^3 \left(0 \leq x \leq -\frac{D}{2r_2}\right) \tag{2}$$

where D is the effective diameter of the lens, y is the displacement in the direction of an optical axis of an aspherical shape as expressed by a rectangular coordinate system having the origin at the vertex of the second surface and normalized by $r_2$, and x is the displacement in a direction normal to the optical axis and also normalized by $r_2$.

2. The aspherical lens of claim 1 further satisfying the following chart:
 $r_1$: 138.450
 $d_1$ 16.800
 $n_1$: 1.51633
 $\nu_1$: 64.1
 $r_2$: −78.939
 K: 1.0
 $A_4$: $0.5123 \times 10^{-6}$
 $A_6$: $0.1160 \times 10^{-9}$
 $A_8$: $-0.7421 \times 10^{-13}$
 $A_{10}$: $0.2134 \times 10^{-16}$
 f:100.000
 $F_{NO}$:1:1.33
 $\omega$: ±18°
 $r_2/r_1$: −0.57
where $d_1$: the inter-surface distance of the lens;
$n_1$: the refractive index of the lens at d-line;
$\nu_1$: the Abbe number of the lens;
K, Ai: the aspherical coefficients;
f: the focal length of the lens;
$F_{NO}$: the F number; and
$\omega$: the half angle of view.

3. The aspherical lens of claim 1 further satisfying the following chart:

$r_1$: 156.588
$d_1$: 28.400
$n_1$: 1.51633
$\nu_1$: 64.1
$r_2$: $-72.276$
K: 1.0
$A_4$: $0.4960 \times 10^{-6}$
$A_6$: $0.5584 \times 10^{-10}$
$A_8$: $0.6669 \times 10^{-14}$
$A_{10}$: $0.2480 \times 10^{-18}$
f: 100.000
$F_{NO}$: 1:1.00
$\omega$: $\pm 25°$
$r_2/r_1$: $-0.46$ where
$d_1$: the inter-surface distance of the lens;
$n_1$: the refractive index of the lens at d-line;
$\nu_1$: the Abbe number of the lens;
K, Ai: the aspherical coefficients;
f: the focal length of the lens;
$F_{NO}$: the F number; and
$\omega$: the half angle of view.

4. The aspherical lens of claim 1 further satisfying the following chart:

$r_1$: 185.340
$d_1$: 36.600
$n_1$: 1.58913
$\nu_1$: 61.0
$r_2$: $-80.040$
K: 1.0
$A_4$: $0.3715 \times 10^{-6}$
$A_6$: $0.2021 \times 10^{-10}$
$A_8$: $0.6027 \times 10^{-14}$
$A_{10}$: $0.1153 \times 10^{-18}$
f: 100.000
$F_{NO}$: 1:0.83
$\omega$: $\pm 30°$
$r_2/r_1$: $-0.43$ where
$d_1$: the inter-surface distance of the lens;
$n_1$: the refractive index of the lens at d-line;
$\nu_1$: the Abbe number of the lens;
K, Ai: the aspherical coefficients;
f: the focal length of the lens;
$F_{NO}$: the F number; and
$\omega$: the half angle of view.

* * * * *